Figure 1:
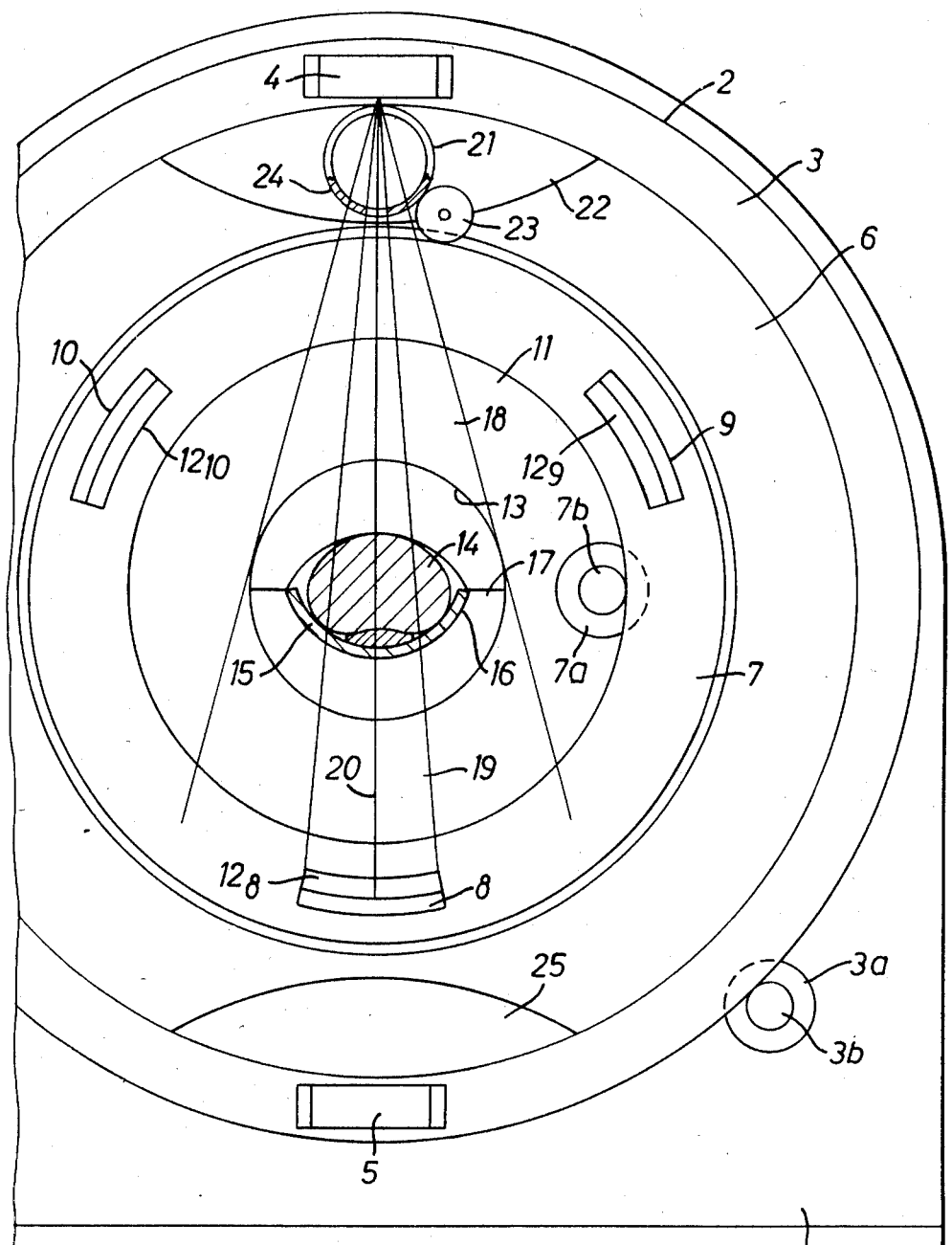

United States Patent [19]

Oliver

[11] Patent Number: 4,578,801

[45] Date of Patent: Mar. 25, 1986

[54] RADIOGRAPHY

[75] Inventor: Colin C. Oliver, Slough, England

[73] Assignee: EMI Limited, Hayes, England

[21] Appl. No.: 832,378

[22] Filed: Sep. 12, 1977

[30] Foreign Application Priority Data

Sep. 23, 1976 [GB] United Kingdom ............... 39461/76

[51] Int. Cl.⁴ ............................................. A61B 6/00
[52] U.S. Cl. ......................................... 378/19; 378/4
[58] Field of Search ................. 250/445 T; 378/4, 19, 378/15

[56]     References Cited
U.S. PATENT DOCUMENTS 4,010,370  3/1977  Le May ............................... 250/445
4,031,395  6/1977  Le May ........................... 250/445 T Primary Examiner—Craig E. Church
Attorney, Agent, or Firm—Cooper, Dunham, Clark, Griffin & Moran

[57]     ABSTRACT

A radiographic apparatus contains at least one source and at least one detector bank mounted on respective concentric annular rings; the patient's body being disposed inside the smaller ring. The rings are rotated in opposite directions and at such respective angular velocities that the effect of a lateral sweep of the detectors and source across the body is achieved with purely rotational movements. Advantageously, one ring carries two sources disposed diametrically opposite one another and the other ring carries three banks of detectors distributed equi-angularly therearound.

12 Claims, 2 Drawing Figures

RADIOGRAPHY

The present invention relates to radiography and it relates especially to that branch of radiography which has become known as computerised tomography.

The object of computerised tomography is to produce a representation of the variation of absorption (or transmission) of X-radiation over a slice disposed cross-sectionally of a body under examination. Techniques for performing computerised tomography are disclosed, for example, in U.S. Pat. No. 3,778,614.

The present invention aims at providing apparatus for performing computerised tomography, which does not require a reciprocating motion of a source and one or more detectors, relative to the body under examination, which motion is usually employed in current computerised tomographic apparatus.

According to the invention there is provided radiographic apparatus comprising at least one source of a distribution of X-radiation arranged to irradiate a cross-sectional region through a patient position, at least one array of detectors sensitive to said radiation and arranged to receive radiation emergent from said region, and means for counter-rotating the source and the array, about an axis passing through said region, at respective angular rates such that the effect of a substantially linear traverse of said source and said array relative to said region is achieved.

Figure 2:
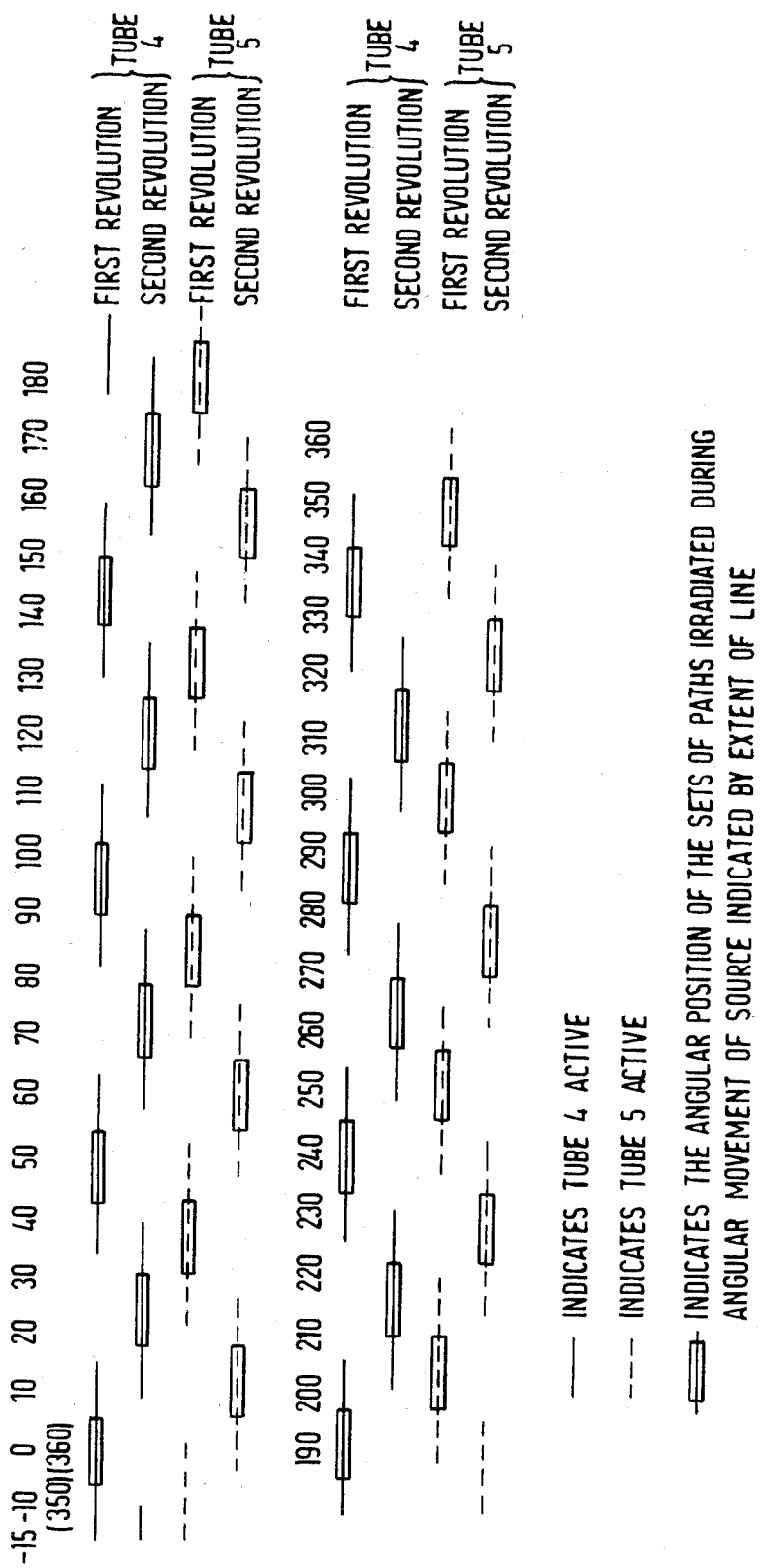

In order that the invention may be clearly understood and readily carried into effect, an embodiment thereof will now be described by way of example only, with reference to the accompanying drawings of which:

FIG. 1 shows, in end elevational view, apparatus according to one example of the invention and FIG. 2 shows a timing diagram explanatory of the operation of the apparatus shown in FIG. 1.

Referring now to the drawings, a main frame 1 is secured to the floor of a building. This frame is formed with a circular aperture 2 dimensioned to accomodate a first ring member 3 which carries first and second substantially identical X-ray tubes 4 and 5; the tubes being disposed diametrically opposite one another. The ring member 3 is rotatably supported on a bearing surface formed on a stationary ring member 6 which is supported by the main frame 1.

Disposed inside the ring member, and mounted concentrically therewith, is another ring member 7 which carries three detector arrays 8, 9 and 10. Each array contains thirty-six detectors and subtends an angle of 12° at the source tube position. The ring member 7 is rotatably supported on a bearing surface formed on a stationary ring member 11 which is supported by the main frame 1. The circular inner periphery 13 of the ring member 11 defines the outer bounds of a patient position.

In this example, a patient's body is shown in cross-section at 14, the body being supported supine on a curved platter 15. The platter 15 is itself supported in a correspondingly curved groove 16 formed in a table 17 which is supported by the main frame 1. Means, for example of the kind disclosed in U.S. Pat. No. 4,034,224 are provided for moving the platter 15 along the groove 16 in a direction perpendicular to the plane of FIG. 1, so as to position a desired cross-sectional slice of the body 14 so that it can be irradiated by the source tubes 4 and 5. These tubes are each arranged to produce a substantially planar, fan-shaped spread of X-radiation, having a fan-angle of thirty degrees in this example, the spreads of radiation being disposed substantially parallel to the plane of FIG. 1.

Disposed between each detector array and the body, and fixedly secured to the arrays are respective banks $12_8$, $12_9$, $12_{10}$ of slanting collimators of the kind described in U.S. Application Ser. No. 772,688 filed Feb. 28, 1977, now U.S. Pat. No. 4,101,768. These collimator banks are provided for the purpose of reducing the effects of scattered radiation from within the body 14, but they do not restrict the radiation impinging on the detectors to a narrow beam.

The spread of radiation generated by the source tube 4 is shown at 18 and it will be seen that the dimensions of the apparatus are such that the extreme beams of the spread 18 are tangential to the circular surface 13 which bounds the patient position.

It has previously been mentioned that the ring members 3 and 7 are rotatably mounted, and means, such as respective electric motors $3a$ and $7a$ driving respective gear wheels $3b$ and $7b$ which mesh with gear teeth formed all around the peripheries of the members 3 and 7, are provided for rotating these two ring members in opposite directions and at different angular velocities. With the dimensions used in this example, wherein the ratio of the radii of circle 13 to that of the focus of the junctions between the detector arrays 8, 9, 10 and their respective collimator banks to that of the inner surface of member 3 is approximately 2:5:8, the angular velocity of the ring member 7 is about 50% higher than that of member 3. These dimensions and rates are chosen so that, for example as shown in FIG. 1, tube 4 irradiates the array 8 whilst the two components sweep from left to right across the patient position, (assuming that ring member 3 rotates in a clockwise direction) thus causing, in effect, a 12° sector of the radiation to sweep across the patient position whilst remaining at the same angular orientation with respect thereto. Clearly the 12° sector which, at any time, is irradiating the array 8 will be selected from different angular regions of the 30° spread 18.

It will be appreciated that the position shown in FIG. 1 corresponds to the central point of the aforementioned sweep; the 12° sector defined by the array 8 being shown at 19 and, of course, being centrally disposed within the 30° sector 18. The central beam 20 of the sector is vertical and impinges on a central detector in the array 8.

Considering clockwise movement of the ring member 3 and anti-clockwise movement of the ring member 7, it will be observed that, provided the two motions are correctly related, the aforementioned central detector will continue to provide output signals relating to beams parallel to the beam 20. Similar considerations apply to the other detectors in the array 8 so it will be observed that, in effect, thirty-six beams disposed within the 12° sector are swept across the patient position, each beam remaining, throughout the sweep, substantially parallel to its position at the commencement of the sweep. The beams give rise to output signals from the detectors which can be identified, in known manner, by means of timing pulses generated in response to the scanning movements of the ring members 3 and 7. The timing pulses can be derived from suitable photocell/detector and graticule arrangements which can take the general form shown and described in U.S. Pat. No. 4,002,910.

It will be appreciated that, as described thus far the patient position receives radiation over 30° whereas only a 12° sector of the radiation is detected at any one time. This can be mitigated, as shown in FIG. 1, by providing a rotatable collar 21 which is mounted on a support 22 secured to the source ring 3. The collar is rotated by means of a gearing arrangement including a gear wheel 23 (also carried on support 22) which is driven by teeth (not shown) formed on the outer periphery of ring 7. The collar 21 includes an apertured skirt, shown in part at 24, which projects into the radiation beam and obscures all except the desired 12° sector which, for the time being, is aligned with a detector array.

The collar 21 is tilted with respect to the plane of investigation so that parts of the skirt 24 for the time being disposed directly in front of the source 4 do not get in the way of the radiation emitted from the source. By this means, the apertures at the side of the skirt 24 more remote from the source act as collimators and sweep across between the source and the body in synchromism with the source and detector movements so as to pass, at all times, only radiation which will fall upon detectors. The effect of the gearing of wheel 23 is such that the collar 21 rotates anti-clockwise, i.e. in the same sense as the detector ring 7. A similar arrangement 25, not shown in detail is, of course, provided for source 5.

If desired the individual collars such as 21 may be disposed to surround the sources 4 and 5 and in that case, there is no need for the collars to be tilted.

Another possible arrangement is to have 12° selecting collimators mounted on a ring, concentric with members 3 and 7, which is rotated at a suitable speed, relative to the sources and detectors, to achieve the desired object of restricting the radiation impinging on the patient position to that which will give rise to usefully detected information. In this case, of course, the components 21-25 are not necessary.

It will be appreciated that, in the position shown in FIG. 1, the tube 5 is not rendered operative because, if it were, it would only irradiate the reverse side of the array 8. However, as the scanning motions described above proceed, the array 8 moves out of the way of the radiation from source tube 5 and the array 9 is positioned to receive radiation from tube 5 after such radiation has passed through the patient position. Then commences another sweep of radiation across the body, the radiation this time emanating from the tube 5 and being detected by the array 9. At some stage during this second sweep, the array 9 will move into the path of radiation emitted by the tube 4, and this tube is then turned off. The next sweep is produced by the co-operation of source tube 4 with the third detector array 10, the following sweep by the co-operation of source tube 5 with array 8 and so-on. If two revolutions around the patient position are effected by the ring member 3, it has been discovered that the body can be irradiated along 540 sets of parallel paths through the patient position, the paths being distributed at intervals of one-third of a degree around the patient position, and moreover that each path is irradiated twice.

The output signals corresponding to these paths are sufficient to permit, on being suitably processed, the evaluation of the absorption (or transmission) coefficient at each of many locations distributed over the irradiated cross-sectional slice of the body 14. The processing may be effected for example, by means of either of the techniques described in U.S. Pat. Nos. 3,778,614 and 3,924,129.

Turning now to the timing diagram of FIG. 2, this shows how the various paths are irradiated with the apparatus as described above. The angles represent angular positions of the two X-ray sources 4 and 5, with the position of source 4 shown in FIG. 1 constituting the 0° position. The solid lines represent the tube 4 being operative and the dashed lines represent the tube 5 being operative; the gaps, of course, representing rotation carried out whilst the respective tubes are inoperative.

The boxes superimposed on the lines represent the angular disposition, with respect to the patient position, of the actual group of paths detected by the respective detector arrays at the appropriate times. It can be seen that the tubes 4 and 5 have to be turned on and off in exact anti-phase with one another and this is an advantageous arrangement in that it tends to stabilise the load demands placed upon the H.T. supplies used to apply potential to the tubes.

It is found, and this can be seen from FIG. 2, that each tube is rendered active for 30° of rotation of member 3, then inactive for 18° of rotation and so-on; the tubes being as aforementioned energised in exact anti-phase with one another, although because of the unequal mark-to-space ratio of the movements in the energised and non-energised conditions, overlap periods, when both tubes are energised, occur. Thus, referring to FIG. 1, tube 4 is energised in its initial (0°) position and will remain energised until it has been rotated through 15°. The tube 5, on the other hand, is not energised while in its 180° position, but is energised when it assumes the 189° position, i.e. after the member 3 has been rotated through 9°, and remains so until the 219° position, when the member 3 has been rotated through 39° from the initial position, when tube 5 is again de-energised. Tube 4, having been de-energised after said 15° of rotation, is re-energised when it assumes the 33° position. This procedure continues throughout the scanning operation.

The purpose of the collimators in the banks 12, as aforesaid, is to reduce the effects of scattering of the radiation by the body 14, so that the output signals provided by the detectors relate to the radiation transmitted thereto along substantially linear paths through the patient position. These collimators can be omitted if desired, or they may be replaced by an alternative arrangement which is capable of allowing for the relative angular movement which occurs between the sources and the detector arrays whilst the aforementioned sweeps are effected (i.e. during the periods in which the tubes are energised).

Alternatively, if it is desired to use collimators which are longer, measured in a radial direction, than those in bank 12, the source tube 4, 5 and/or detector arrays 8-10 can be arranged to perform a rocking motion to tend to eliminate said relative angular movement. If such movement is imparted to the sources, the added benefit is obtained that they need only provide 12° spreads of radiation instead of the 30° spread required in the arrangement described with reference to FIG. 1. This reduces the amount of radiation to which the patient is subjected.

Although the invention has been described with regard to an embodiment in which two X-ray tubes and three detector arrays are used, this is by no means the only configuration which can be employed. For example three source tubes can be used in conjunction with three or four detector arrays. Moreover, the detector arrays could be mounted on member 3 and the source tubes on member 7.

What I claim is:

1. A method of scanning an area of interest within a transverse body plane comprising the steps of: continuously rotating a source of penetrating radiation and a radiation detector array in opposing directions about said area of interest to provide a series of parallel radiation beam paths from said source to said detector array over a plurality of angular positions through said area.

2. A method of scanning an area of interest within a transverse body plane comprising the steps of: continuously moving in arcuate paths in opposing directions around said area of interest a source of penetrating radiation and a radiation detector array to provide a series of parallel radiation beam paths from said source to said detector array over a plurality of angular positions through said area.

3. A method of scanning an area of interest within a transverse plane of a patient's body comprising the steps of:
continuously moving a source of penetrating radiation and each detector of a radiation detector array in opposite directions along respective orbits each of which surrounds said area of interest at least halfway, to cause the detector array to receive radiation from the source along sets of radiation beam paths;
wherein the paths within a set are parallel to each other and the paths of different sets are at an angle to each other; and
generating detector output signals which correspond to said paths and are sufficient to permit finding the absorption coefficient at each of many locations distributed over said area of interest, and producing therefrom a representation of said area of interest.

4. A medical X-ray machine comprising:
at least one source of a fan-shaped distribution of X-radiation directed at a cross-sectional slice of a patient's body;
at least one array of detectors of X-radiation emergent from the slice; and
means for continuously moving the source along a source orbit surrounding the slice and for concurrently continuously moving the array of detectors in the opposite direction along a detector orbit also surrounding the slice; the respective continuous movements of the source and of the array of detectors causing each individual detector in the array to receive radiation emergent from the slice along a plurality of sets of substantially parallel paths, each set including paths distributed across substantially the full width of said slice and oriented at a respective angle in the body slice; the radiation pertaining to a plurality of said sets being simultaneously received by respective detectors of the array each time the source and the array of detectors are disposed at opposing sides of the slice and sweep there-across in the same lateral direction as a result of their counter-rotation about their respective orbits.

5. A medical X-ray machine as in claim 4 wherein the source orbit and the detector orbit are concentric circles centered at an axis passing through the patient, one of the source and array of detectors moves in the clockwise direction and the other in the counterclockwise direction, and the motions are at different angular velocities.

6. A medical X-ray machine as in claim 5 in which the detector orbit has a diameter less than that of the source orbit.

7. Computerized tomographic apparatus including first support means supporting at least one source of penetrating radiation, first scanning means causing angular movement of said first support means, and with it said source, around a patient position, said source being disposed on said first support means to irradiate the patient position during the angular movement, detector means including a plurality of detector devices sensitive to said radiation for detecting radiation emergent from the patient position, the irradiation of the patient position and the detection of the radiation being effected in a common plane, the detector means including further detector devices in addition to those receiving said radiation at any one time; second support means, including a ring surrounding said patient position supporting said detector means with said further detector devices and said first-mentioned detector devices symmetrically distributed around said ring and with the detector devices of said detector means being disposed closer to said patient position than is said source, means causing relative movement between the source and the detector means to scan the radiation relative to the patient position and the detector means, and means constraining said further detector devices to allow free passage of said radiation to said first-mentioned detector devices.

8. Apparatus according to claim 7 wherein said first support means comprises a ring surrounding and concentric with the ring supporting said detector devices.

9. Apparatus according to claim 8 wherein said rings supporting, respectively, said source and said detector devices, rotate in opposite directions and at different angular velocities around the patient position, causing, during part of said movement, said source and said first-mentioned detector devices to move together across said patient position, with each of said first-mentioned detector devices receiving radiation from said source along a plurality of substantially parallel beam paths across said patient position during said part of said movement.

10. Apparatus according to claim 9 wherein said first support means supports two sources disposed diametrically of the ring and said detector means comprises three angularly spaced arrays of detector devices centered at 120° intervals around the ring which supports them.

11. Apparatus according to claim 10 wherein said means constraining said further detectors comprises means for rotating the two support rings at respective angular velocities causing the space between the two detector arrays for the time being constituting said further detector devices to be presented to radiation directed towards the detector array for the time being constituting said first-mentioned detector devices.

12. Apparatus according to claim 11 wherein said two sources are caused to generate X-radiation in antiphase.

* * * * *